United States Patent [19]

Arduengo

[11] Patent Number: 4,710,576

[45] Date of Patent: Dec. 1, 1987

[54] THERMOCHROMIC ARSENIC AND ANTIMONY COMPOUNDS

[75] Inventor: Anthony J. Arduengo, Wilmington, Del.

[73] Assignee: E. I. Du Pont de Nemours and Company, Wilmington, Del.

[21] Appl. No.: 830,840

[22] Filed: Feb. 19, 1986

[51] Int. Cl.[4] .............................. C07F 9/68; C07F 9/90
[52] U.S. Cl. ........................................ 556/40; 556/16
[58] Field of Search ............................................ 556/40

[56] References Cited

U.S. PATENT DOCUMENTS

| | | | |
|---|---|---|---|
| 2,976,285 | 3/1961 | Gash | 556/76 X |
| 3,157,682 | 11/1964 | Ramsden | 556/40 X |
| 3,328,444 | 6/1967 | Harrison | 556/76 |
| 3,850,856 | 11/1974 | Dreyfuss | 556/76 X |
| 3,903,120 | 9/1975 | Shook et al. | 556/76 X |
| 4,407,759 | 10/1983 | Crivello | 556/76 |

OTHER PUBLICATIONS

Culley et al., JACS 107 1089 (1985).
Culley, et al., J. Am. Chem. Soc. 106, 1164–1165 (1984).
Stewart, et al., J. Am. Chem. Soc. 107, 5543–5544 (1985).

*Primary Examiner*—Helen M. S. Sneed

[57] ABSTRACT

There are disclosed compounds having the formula

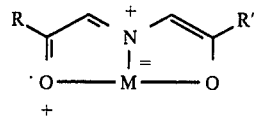

wherein R and R' are selected from the group consisting of
 (a) substituents having the formula $R^1R^2R^3C-$ wherein $R^1$ is H or an alkyl group of 1 to 6 carbon atoms, and $R^2$ and $R^3$ are independently alkyl of 1 to 6 carbon atoms;
 (b) phenyl group;
 (c) phenyl group substituted by Br, Cl, F, alkyl group of 1 to 10 carbon atoms, or alkoxy group of 1 to 10 carbon atoms; and
 (d) an adamantyl group; and M is As or Sb; with the proviso that when R and R' are phenyl or substituted phenyl in which the substituents are in meta or para positions, M is As. Preferably R and R' are the same and are t-butyl, phenyl or adamantyl. The compounds display thermochromic properties.

9 Claims, No Drawings

THERMOCHROMIC ARSENIC AND ANTIMONY COMPOUNDS

BACKGROUND OF THE INVENTION

1. Field of the Invention

This invention relates to arsenic and antimony compounds which display thermochromic properties.

2. References

Culley, et al., *J. Am. Chem. Soc.* 106, 1164–1165 (1984) disclose the synthesis and structure of the first 10-P-3 species, 5-aza-2,8-dioxa-3,7-di-tert-butyl-1-phosphabicyclo[3. 3.0]octa-2,4,6-triene [ADPO](in the publication the compound is referred to as a diene).

SUMMARY OF THE INVENTION

The present invention provides novel compounds having the formula

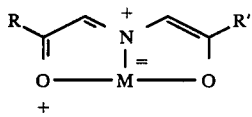

wherein R and R' are independently selected from the group consisting of
(a) substituents having the formula $R^1R^2R^3C-$ wherein $R^1$ is H or an alkyl group of 1 to 6 carbon atoms, and $R^2$ and $R^3$ are independently alkyl of 1 to 6 carbon atoms;
(b) phenyl group;
(c) phenyl group substituted by Br, Cl, F, alkyl group of 1 to 10 carbon atoms, or alkoxy group of 1 to 10 carbon atoms; and
(d) the adamantyl group;
and M is As or Sb; with the proviso that when R and R' are phenyl or substituted phenyl in which the substituents are in meta or para positions, M is As. The compounds display thermochromic properties.

DETAILED DESCRIPTION OF THE INVENTION

The compounds of the invention can be prepared by reacting the appropriate 3-aza-1,5-di(substituted)pentane-1,5-dione ligand,

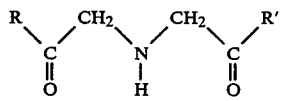

wherein R and R' are the same as previously defined, a suitable tertiary amine base and either antimony trihalide or arsenic trihalide in a solvent such as tetrahydrofuran at a temperature of about −30° C. to about −78° C., most preferably about −78° C. Suitable tertiary amine bases include triethylamine and tri-n-butylamine with triethylamine being preferred. Temperatures lower than −78° C. can be employed by using a polar aprotic solvent with a lower freezing point. The symmetrical ligands are prepared by reacting the appropriate bromomethyl alkyl or aryl ketone with benzylamine in a suitable solvent to produce the hydrobromide salt of the corresponding N-benzylated ligand from which the benzyl group is removed by hydrogenolysis to give the hydrobromide salt of desired ligand. Suitable solvents include benzene, toluene, ether, dioxane and glyme but benzene is preferred. The unsymmetrical ligands (R≠R') can be prepared by suitable modification of the foregoing procedure according to techniques well known in the art.

Hydrogenolysis can be conducted in a suitable solvent, such as methanol which is preferred, at ambient or elevated temperatures but ambient temperature is preferred. Pressure is not critical and both high and low pressures can be used but a pressure of about 101 kPa (14.7 psi) is preferred. Preferably, the catalyst is palladium on charcoal, most preferably about 5% palladium by weight on charcoal. The procedure for hydrogenolysis of benzylammonium salts is well known; see Buehler, et al., *Survey of Organic Synthesis,* (New York, Interscience), vol. 1, pp. 430–433.

The ligand can be liberated from the salt by neutralization with a suitable base. In general, neutralization should be effected with a base whose conjugate acid has a higher pKa than the protonated ligand. Suitable bases include sodium phosphate and sodium carbonate with sodium phosphate being preferred. The resulting crude ligand can be purified by sublimation or crystallization from suitable solvents, such as benzene, toluene, cyclohexane and hexane.

The compounds of the invention have the formula previously given herein. Preferably, R is t-butyl, phenyl or adamantyl. The structure and preparation of the compound wherein M is As and R is t-butyl are described by Culley, et al., *J. Am. Chem. Soc.* 107, 1089–1090 (1985). The structure and preparation of the compound wherein M is Sb and R is t-butyl are described by Stewart, et al., *J. Am. Chem. Soc.* 107, 5543–5544 (1985). The compounds of the invention are sensitive to moisture and oxygen with the arsenic compounds being less sensitive than the antimony compounds. Due to this sensitivity, the compounds of the invention should be stored and handled in the absence of oxygen and moisture. The compounds of the invention undergo a thermochromic change at various temperatures depending upon the values of M and R. The thermochromic change occurs at the melting point and is reversible. A sample of a compound of the invention sealed in a glass tube or other suitable container would make a convenient temperature indicator in a useful temperature range. Thermochromic indication of temperature has numerous applications which include measurement of surface temperatures, sterilization indicators for medical devices, and measurement of excessive temperatures to indciate faulty operating conditions.

The invention is further illustrated by the following examples in which percentages are by weight and temperatures are in degrees Celsius unless otherwise stated. In the examples, the symbol "Ph" represents a phenyl group.

EXAMPLE 1

5-Aza-2,8 -dioxa-3,7-di-tert-butyl-1 -arsabicyclo[3.3. 0]octa-2,4,6-triene

A. Preparation of 5-Aza-5-benzyl-2,2,8,8-tetramethylnonane-3,7-dione hydrobromide A 12-liter 3-neck flask fitted with a mechanical stirrer and condenser was charged with 8 L of benzene and 1278.0 g (7.14 mol) of 1-bromo-3,3-dimethyl-2-butanone. The flask was purged with nitrogen and then 765.1 g (7.14 mol) of benzylamine were added. The resulting mixture was heated at reflux for 2 days and then allowed to cool to ambient temperature. Solids were collected from the mixture by filtration and washed with water (two 1-liter portions) to give 850 g of the desired crude material which was then recrystallized from ethanol to give 780 grams of the benzylated amine hydrobromide(57%): m.p.=214°-215°; $^1$H NMR (CDCl$_3$) 1.14 (s, 18 H, CH$_3$), 4.63 (d, 4 H, COCH$_2$), 4.67 (d, 2 H, PhCH$_2$), 7.47 (m, 3 H, Ar), 7.67 (m, 2 H, Ar).

B. Preparation of 5-Aza-2,2,8,8-tetramethylnonane-3,7-dione hydrobromide

A 10-liter polyethylene vessel equipped with a mechanical stirrer was charged with 8 L of methanol and 664 g (1.68 mol) of the benzylated amine hydrobromide prepared substantially according to part A of this Example. The resulting mixture was purged with nitrogen for 10 minutes and then 10 g of 5% palladium on charcoal was added to the mixture. Hydrogen was then bubbled through the resulting mixture for 18 hours. Next the palladium/charcoal was removed by filtration and solvent was removed by evaporation under reduced pressure. The resulting residue was recrystallized from ethanol to give 466 g (91%) of the desired amine hydrobromide: m.p.=240°-242°; $^1$H NMR (DMSO-d$_6$) 1.10 (s, 18 H, CH$_3$), 3.20 (s, 2 H, NH$_2$), 4.20 (s, 4 H, COCH$_2$).

C. Preparation of 5-Aza-2,2,8,8-tetramethylnonane-3,7-dione

The amine hydrobromide (14.71 g, 0.05 mol) prepared substantially as described in part B of this Example was dissolved in 210 mL of water and deoxygenated by purging with nitrogen. To a 1-liter 3-neck flask were added 22.81 g of Na$_3$PO$_4$.12H$_2$O (0.06 mol) which was dissolved in a mixture of 150mL of water and 150mL of CH$_2$Cl$_2$. The resulting mixture was purged with nitrogen for 5 minutes and then cooled with an ice bath. The solution of amine hydrobromide was added dropwise over 1 hour to the solution of sodium phosphate while it was stirred. The resulting mixture was stirred for an additional 2 hours at 5° and then allowed to separate into layers. The CH$_2$Cl$_2$ layer was separated leaving an aqueous layer which was washed with three 10-15 mL portions of CH$_2$Cl$_2$. The CH$_2$Cl$_2$ layers were combined, washed with water (three times with 10-15 mL portions), dried and evaporated to give a residue. This residue was sublimed under reduced pressure to give 9.7 g (91%) of the desired amine: m.p.=61°-62°; $^1$H NMR (CDCl$_3$) 1.15 (s, 18 H, CH$_3$), 2.44 (s, 1 H, NH), 3.61 (s, 4 H, COCH$_2$).

D. Preparation of 5-Aza-2,8-dioxa-3,7-di-tert-butyl-1-arsabicyclo[3.3.0]octa-2,4,6-triene Under nitrogen, 3.41 g (16.0 mmol) of the amine prepared substantially according to part C of this Example in 30 mL of tetrahydrofuran (THF) were added to a stirred solution of AsCl$_3$ (2.90 g, 16.0 mmol) in 100 mL of THF held at −78°. When the addition was completed, triethylamine (6.8 mL, 48.7 mmol) in 30 mL of THF was added dropwise. After three hours the resulting reaction mixture was warmed to ambient temperature. Upon warming the solution turned a pale yellow. Solvent was removed under reduced pressure to yield a light yellow solid. This solid was washed with pentane to give a solid (crude triethylamine hydrochloride) and a yellow-green solution. The volume of pentane in the solution was decreased under reduced pressure to bring about crystallization. The resulting product, 5-aza-2,8-dioxa-3,7-di-tert-butyl-1-arsabicyclo[3.3.0 ]octa-2,4,6-triene, was recrystallized from pentane at −25° to give light green crystals (80%): m.p.=124°-126°; EI mass spectrum (70 eV) at m/z=285; $^1$H NMR (CD$_2$Cl$_2$) 1.31 (s, 9 H), 7.90 (s, 1 H); proton decoupled $^{13}$C NMR (CD$_2$Cl$_2$) 28.3 (CH$_3$), 36.3 (C(CH$_3$)$_3$), 113.6 (CN), 174.8 (CO); $^{15}$N NMR (CD$_2$Cl$_2$) −96.0 (ref. NH$_4$$^{15}$NO$_3$).

EXAMPLE 2

5-Aza-2,8 -dioxa-3,7 -di-tert-butyl-1 -stibabicyclo [3.3.0]octa-2,4,6 -triene

Under nitrogen, 5-aza-2,2,8,8-tetramethylnonane-3,7-dione (3.41 g, 16.0 mmol), prepared substantially according to the procedure given in Example 1, in 40 mL of THF was added dropwise to a stirred solution of SbCl$_3$ (3.65 g, 16.0 mmol) in 50 mL of THF held at −78°. After the addition was completed, triethylamine (9.5 mL, 68 mmol) in 30 mL of THF was added dropwise. After three hours the resulting reaction mixture was warmed to ambient temperature where the mixture gradually turned from green to dark red-brown. Solvent was evaporated under reduced pressure to yield a dark yellow solid which was then washed with pentane to give a light yellow solid (crude triethylamine hydrochloride) and a dark red-brown solution. The volume of pentane in the solution was decreased by evaporation under reduced pressure to induce crystallization. The product was crystallized at −25° as a yellow-green solid (70%): m.p.=116°; EI mass spectrum (70 eV) at m/z=331; $^1$H NMR (CD$_2$Cl$_2$) 1.39 (s, 9 H), 8.46 (s, 1 H); proton decoupled $^{13}$C NMR (CD$_2$Cl$_2$) 28.8 (CH$_3$), 38.0 (C(CH$_3$)$_3$), 117.8 (CN), 176.7 (CO); $^{15}$N NMR (CD$_2$Cl$_2$) −90.9 (ref. NH$_4$$^{15}$NO$_3$).

EXAMPLE 3

5-Aza-2,8-dioxo-3,7-di(1-adamantyl)-1-stibabicyclo[3.3.0]octa-2,4,6 -triene

A. Preparation of 3-Aza-3-benzyl-1,5-di(1-adamantyl)pentane-1,5-dione hydrobromide A 3-liter 3-neck flask fitted with a condenser and mechanical stirrer was charged with 1-adamantyl bromomethyl ketone (77.1 g, 0.3 mol) and 1.2 L of dry benzene. Benzylamine (32.5 g, 0.3 mol) was added. The flask was purged with nitrogen and its contents were heated to reflux and maintained at reflux temperature for 48 hours. Next the resulting reaction mixture was filtered to separate out suspended solids which were then washed with 500 mL of benzene. The solids were next thoroughly washed with 1 L of water in a blender and dried under reduced pressure. Additional product was obtained by evaporation of the benzene filtrate. Recrystallization of the solid from ethanol yielded 20.9 grams of the desired benzylated amine hydrobromide: m.p.=218°-220°; $^1$H NMR (CD$_2$Cl$_2$) 1.69 (m, 12 H, CH$_2$), 1.77 (s, 12 H, CH$_2$), 2.04 (s, 6 H, C$_3$CH), 4.69 (dd, 4 H, COCH$_2$), 4.70 (d, 2H, PhCH$_2$), 7.45 (m, 3 H, Ar), 7.68 (m, 2 H, Ar).

B. Preparation of 3-Aza-1,5-di(1-adamantyl)pentane-1,5-dione hydrobromide

A one-liter heavy walled Erlenmeyer flask was charged with 37.7 g (69.8 mmol) of the benzylated amine hydrobromide prepared substantially according to part A of this Example and 800 mL of methanol. The resulting methanol suspension was purged with nitrogen for 10 minutes, and then 0.66 g of 5% palladium on charcoal was added. Hydrogen was bubbled through the resulting suspension for 18 hours. The palladium/charcoal was removed by filtration and the resulting filtrate was evaporated to give 23.1 g (74%) of the desired amine hydrobromide: m.p.=282°–284° (recrystallized); $^1$H NMR (DMSO-D$_6$) 1.68 (m, 6 H, CH$_2$), 1.76 (m, 6 H, CH$_2$) 2.00 (m, 3 H, C$_3$CH), 4.20 (s, 2 H, COCH$_2$).

C. Preparation of 3-Aza-1,5-di(1-adamantyl)pentane-1,5-dione

A one-liter 3-neck flask was charged with 200 mL of water, 150 mL of CH$_2$Cl$_2$ and 14.4 g (31.6 mmol) of the amine hydrobromide prepared substantially according to part B of this Example. The resulting mixture was purged with nitrogen for 15 minutes and cooled in an ice bath. A solution of Na$_3$PO$_4$.12H$_2$O (18.0 g, 47.0 mmol) in 150 mL of water was added to the stirred mixture over 15 minutes. The resulting mixture was stirred at 0° for 2.5 hours. After stirring was stopped, a CH$_2$Cl$_2$ layer formed, was separated, washed (three 50 mL portion of water), and dried over MgSO$_4$. The CH$_2$Cl$_2$ was evaporated and the resulting residue was recrystallized from cyclohexane to give 11.0 g (93%) of the desired amine: m.p.=134°–136°; $^1$H NMR (CD$_2$Cl$_2$) 1.74 (m, 12 H, CH$_2$), 1.81 (m, 12 H, CH$_2$), 2.04 (m, 6 H, C$_3$CH), 2.18 (s, 1 H, NH), 3.57 (s, 4 H, COCH$_2$).

D. Preparation of 5-Aza-2,8-dioxa-3,7-di(1-adamantyl)-1-stibabicyclo[3.3.0]octa-2,4,6-triene Under nitrogen, 2.01 g (5.45 mmol) of the amine, prepared substantially according to the procedure in part C of this Example, in 20 mL of THF were added dropwise to a stirred solution of SbCl$_3$ (1.24 g, 5.44 mmol) in 50 mL of THF held at −78°. When the addition is completed, triethylamine (1.65 g, 16.3 mmol) in 15 mL of THF was added dropwise to the resulting mixture over 0.5 hour. The resulting mixture was stirred at −78° for 1 hour and then warmed to ambient temperature. The THF was removed by evaporation under reduced pressure to give a yellow solid which was then extracted with CH$_2$Cl$_2$ (100 mL). The CH$_2$Cl$_2$ was removed by evaporation under reduced pressure to give a residue which was recrystallized from toluene to yield 1.7 g (64%) of the desired octa-2,4,6-triene: m.p.=263°–278°; $^1$H NMR (CD$_2$Cl$_2$) 1.71 (m, 6 H, CH$_2$), 1.96 (m, 6 H, CH$_2$), 2.09 (m, 3 H, C$_3$CH), 8.35 (s, 1 H, CH); proton decoupled $^{13}$C NMR (CD$_2$Cl$_2$) 29.0, 37.3, 39.8 (C$_4$C), 40.9, 117.7 (CN), 176.6 (CO); $^{15}$N NMR (CD$_2$Cl$_2$) -94.5 (ref. NH$_4$$^{15}$NO$_3$).

EXAMPLE 4

5-Aza-2,8-dioxa-3,7-di(1-adamantyl)-1-arsabicyclo[3.3.0]octa-2,4,6-triene

Under nitrogen, 3-aza-1,5-di(1-adamantyl)-pentane-1,5-dione, prepared by a method substantially according to that given in Example 3, (1.85 g, 5.0 mmol) in 15 mL of THF was added dropwise to a stirred solution of AsCl$_3$ (0.91 g, 5.0 mmol) in 50 mL of THF held at −78°. When the addition was completed, triethylamine (1.52 g, 15.0 mmol) in 15 mL of THF was added dropwise to the resulting mixture over 0.5 hour. The resulting mixture was stirred at −78° for 2.5 hours and then warmed to ambient temperature. The mixture was filtered and the resulting THF mother liquor was evaporated to yield 1.37 g of a yellow solid. The solid material from the filtration was washed with 50 mL of water (to remove triethylamine hydrochloride). After a methanol rinse of this material, the solids were combined and dried under reduced pressure. The combined solids were recrystallized from toluene to give 1.4 g (63%) of the desired octa-2,4,6-triene: m.p.=289°–295°; $^1$H NMR (CD$_2$Cl$_2$) 1.78 (m, 6 H, CH$_2$), 2.06 (m, 3 H C$_3$CH), 7.88 (s, 1 H CH); proton decoupled $^{13}$C NMR (CD$_2$Cl$_2$) 28.8, 37.1, 38.4 (C$_4$C), 40.6, 113.6 (CN), 174.9 (CO); $^{15}$N NMR (CD$_2$Cl$_2$) -96.1 (ref. NH$_4$$^{15}$NO$_3$).

EXAMPLE 5

5-Aza-2,8-dioxa-3,7-diphenyl-1-arsabicyclo[3.3.0]octa-2,4,6-triene

A. Preparation of 3-Aza-3-benzyl-1,5-diphenylpentane-1,5-dione hydrobromide A 3-liter 3-neck flask fitted with a condenser and mechanical stirrer was charged with phenyl bromomethyl ketone (200 g, 1 mol) and one liter of dry benzene under an atmosphere of nitrogen. An additional 500 mL of benzene and 107 g (1 mol) of benzylamine were added with stirring. The resulting solution was diluted with another 700 mL of benzene and heated to reflux. Considerable solid precipitated from the solution before heating, thereby making stirring difficult. The resulting mixture was refluxed for 40 hours after which the initial scale-like solid was replaced by a microcrystalline solid. The mixture was cooled and filtered yielding a solid which was washed with 200 mL of benzene. The benzene was removed by evaporation. The resulting solid was washed with 1000 mL of water to remove benzylamine hydrobromide. The remaining insoluble material was recrystallized from acetonitrile/water to give 59.8 g of the desired benzylated amine hydrobromide: m.p.=198°–204° (dec.); $^1$H NMR (DMSO-d$_6$) 4.56 (s, 2 H, CH$_2$Ph), 5.13 (s, 4 H, CH$_2$C=O), 7.34 (m, 3 H, m, p-PhCH$_2$), 7.57 (t, 4 H, m-PhC=O), 7.64 (m, 2 H, o-PhCH$_2$), 7.72 (t, 2 H, p-PhC=O), 7.88 (d, 4 H, o-PhC=O).

B. Preparation of 3-Aza-1,5-diphenylpentane-1,5-dione hydrobromide

In a 1-liter flask 24.82 g (58.5 mmol) of 3-aza-3-benzyl-1,5-diphenylpentane-1,5-dione hydrobromide prepared substantially according to part A of this Example was suspended in 750 mL of methanol. The resulting mixture was purged with nitrogen, and then 0.75 g of 5% palladium on charcoal was added. Hydrogen was bubbled through the mixture for 4 hours during which time all the solids dissolved. The uptake of hydrogen still continued at this point. The resulting methanol solution was filtered through diatomaceous earth filter aid, decreased in volume under reduced pressure, and then placed in a freezer at −25° overnight. Crystals deposited from the solution and were collected by filtration to yield 4.4 g of the desired amine hydrobromide: m.p.=232°–238°; $^1$H NMR (DMSO-d$_6$) 4.88 (s, 4 H, COCH$_2$), 7.61 (m, 4 H, m-Ph), 7.73 (m, 2 H, p-Ph), 8 00 (m, 4 H, o-Ph), 9.58 (s, 2 H, NH$_2$). C. Preparation of 3-Aza-1,5-diphenylpentane1,5-dione A 500-mL 3-neck flask was charged with 100 mL of water, 75 mL of CH$_2$Cl$_2$ and 5.78 g (17.0 mmol) of 3-aza-1,5-diphenylpentane-1,5-dione hydrobromide. The resulting mixture was purged with nitrogen for 15 minutes and cooled in an ice bath. A solution of Na$_3$PO$_4$·12H$_2$O (7.81 g, 21.0 mmol) in 75 mL of water was added to the mixture over 15 minutes with stirring. The resulting mixture was stirred at 5° for one hour. When stirring was ceased, a CH$_2$Cl$_2$ layer formed. This layer was separated, washed with three 50 mL portions of water, and dried over MgSO$_4$. The CH$_2$Cl$_2$ was evaporated off, leaving residue which was recrystallized from toluene to yield 2.6 g (60%) of the desired amine: m.p.=82°-85°; $^1$H NMR (CD$_2$Cl$_2$) 2.69 (br, 1 H, NH), 4.26 (s, 4 H, COCH$_2$), 7.51 (m, 4 H, m-Ph), 7.62 (m, 2 H, p-Ph), 7.97 (m, 4 H, o-Ph).

D. Preparation of 5-Aza-2,8-dioxa-3,7-diphenyl-1-arsabicyclo[3.3.0]octa-2,4,6-triene Under nitrogen, 3-aza-1,5-diphenylpentane-1,5-dione (1.23 g, 5.0 mmol) in 20 mL of THF was added dropwise to a stirred solution of AsCl$_3$ (0.91 g, 5.0 mmol) in 70 mL of THF held at −78°. When the addition was completed, triethylamine (1.52 g, 15.0 mmol) in 15 mL of THF was added dropwise to the resulting mixture over 0.5 hour period. The resulting mixture was stirred at −78° for 2.5 hours and then warmed to ambient temperature. The mixture was filtered and THF was evaporated from the filtrate to yield a red-brown residue. This residue was recrystallized from CH$_2$Cl$_2$ to yield 0.75 g (46%) of the desired octa-2,4,6-triene: m.p.=192°-193°; $^1$H NMR (CD$_2$Cl$_2$) 7.39 (t, 1 H, J$_{HH}$=6.7 Hz, p-Ph), 7.48 (dd, 2 H, J$_{HH}$=6.7 and 8.1 Hz, m-Ph), 7.88 (d,2 H, J$_{HH}$=8.1 Hz, o-Ph), 8.64 (s, 1 H, NCH); proton decoupled $^{13}$C NMR (CD$_2$Cl$_2$) 115.41 (CN), 125.79 (o-C), 129.20 (m-C), 129.73 (p-C), 134.47 (C$_3$C), 162.63 (CO); $^{15}$N NMR (CD$_2$Cl$_2$) -95.5 (ref. NH$_4$$^{15}$NO$_3$).

The octa-2,4,6-trienes prepared in Examples 1-5 were heated and their thermochromism properties were observed. The table below gives the temperature of the most significant color change, yellow to red. The antimony compounds showed a more gradual change from green to yellow over a broad temperature range of from −200° C. to ambient temperature. The compound of Example 2 becomes yellow below its melting point and the compound of Example 3 becomes red at 240°. The changes are all reversible.

TABLE

| | Thermochromic Properties | | |
|---|---|---|---|
| Example | R | M | Color Change (°) |
| 1 | t-butyl | As | 122–124 |
| 2 | t-butyl | Sb | 116 |
| 3 | adamantyl | Sb | 240 |
| 4 | adamantyl | As | 289–295 |
| 5 | phenyl | As | 192–193 |

The invention being claimed is:

1. A compound having the formula

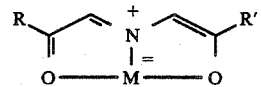

wherein R and R' are selected from the group consisting of
(a) substituents having the formula R$^1$R$^2$R$^3$C— wherein R$^1$ is H or an alkyl groups of 1 to 6 carbon atoms, and R$^2$ and R$^3$ are independently alkyl of 1 to 6 carbon atoms;
(b) phenyl group;
(c) phenyl group substituted by Br, Cl, F, alkyl group of 1 to 10 carbon atoms, or alkoxy group of 1 to 10 carbon atoms; and
(d) an adamantyl group; and M is As or Sb; with the proviso that when R and R' are phenyl or substituted phenyl in which the substituents are in meta or para positions, M is As.

2. A compound of claim 1 wherein R and R' are the same and are t-butyl, phenyl or adamantyl.
3. A compound of claim 2 wherein M is As.
4. A compound of claim 3 wherein R is t-butyl.
5. A compound of claim 3 wherein R is phenyl.
6. A compound of claim 3 wherein R is adamantyl.
7. A compound of claim 2 wherein M is Sb.
8. A compound of claim 7 wherein R is t-butyl.
9. A compound of claim 7 wherein R is adamantyl.

* * * * *